United States Patent

Pangritz

[11] 4,333,333
[45] Jun. 8, 1982

[54] APPARATUS FOR DETERMINING THE BURNING AND/OR GLOWING RATES OF A SMOKABLE ARTICLE

[75] Inventor: Dirk Pangritz, Halstenbek, Fed. Rep. of Germany

[73] Assignee: B.A.T. Cigaretten-Fabriken GmbH, Hamburg, Fed. Rep. of Germany

[21] Appl. No.: 210,050

[22] Filed: Nov. 24, 1980

[30] Foreign Application Priority Data

Nov. 23, 1979 [DE] Fed. Rep. of Germany ....... 2947249

[51] Int. Cl.³ ............................................. G01N 21/72
[52] U.S. Cl. ..................................... 374/8; 250/203R; 318/640; 374/57
[58] Field of Search .......... 73/432 R, 15 R, DIG. 11, 73/35; 250/203 R; 318/640

[56] References Cited

U.S. PATENT DOCUMENTS

| | | | |
|---|---|---|---|
| 448,194 | 3/1891 | Balbin | 73/432 R |
| 2,701,854 | 2/1955 | Carrick | 73/DIG. 11 |
| 3,315,081 | 4/1967 | Williams | 73/35 |
| 3,665,750 | 5/1972 | Dawn et al. | 73/15 |
| 4,163,185 | 7/1979 | Tokuno | 318/640 |

FOREIGN PATENT DOCUMENTS

1757660 5/1971 Fed. Rep. of Germany .

*Primary Examiner*—S. Clement Swisher
*Attorney, Agent, or Firm*—Armstrong, Nikaido, Marmelstein & Kubovcik

[57] ABSTRACT

An apparatus is provided for determining the burning and/or glowing rate of a smokable article. The apparatus comprises a sensor for sensing the incandescent zone of the smokable article and a drive apparatus for moving the sensor along a path parallel to the direction of burning and glowing of the smokable article. A control circuit, including first switches is coupled to the sensor and the drive apparatus, for stopping the drive apparatus and thereby the movement of the sensor when the sensor detects a predetermined radiation intensity and for starting the drive apparatus and thereby the sensor when the sensor detects a radiation intensity other than the predetermined intensity when the first switches are in a first state and for starting the drive apparatus and thereby the movement of the sensor means when the sensor detects a predetermined radiation intensity and for stopping the sensor when the sensor detects a radiation intensity other than the predetermined intensity when the first switches are in a second state.

7 Claims, 3 Drawing Figures

APPARATUS FOR DETERMINING THE BURNING AND/OR GLOWING RATES OF A SMOKABLE ARTICLE

BACKGROUND OF THE INVENTION

1. Field of the Invention

This invention relates to an apparatus for determining the burning and/or glowing rates of a smokable article, with a sensor for the incandescent zone of said article.

2. Description of the Prior Art

The term "smokable article" includes cigars, cigarillos and especially cigarettes. The problems which are significant to these smokable articles will be discussed below in relation to cigarettes.

The tobacco consumed while smoking, that is, during puffing or during the pauses between two puffs, is significant on several accounts: on one hand, conclusions may be drawn regarding product quality and, on the other hand, the consumption represents an important parameter when determining the smoke yields and hence when developing such products.

To-date, the measurements of the amounts of tobacco consumed per unit time have been feasible only at high experimental cost and, as yet, cannot be carried out in routine tests. Use has been made of the glowing rate as a useful parameter; that is, one measures the motion of the roughly conical incandescent zone per unit time when the cigarette is left to itself, i.e., when no inhalation takes place. This is, therefore, the incandescent rate of travel during a single, long pause between two puffs.

The conventional and routine determination of this glowing of travel is obtained by measuring the total duration of glow. That is, a time interval is ascertained which is required by the incandescent zone of a glowing cigarette to cover a precisely defined path length.

Instrumentation for determining glow rate, i.e., the speed of the incandescent zone without any puffing, is known from the German Offenlegungsschrift No. 1,757,660.

Two stationary phototransistors are positioned a predetermined distance apart parallel to the burning cigarette which is held in a fastening means. The two phototransistors each emit a pulse when the incandescent zone of the cigarette passes them. From the time interval between the two pulses and the predetermined distance between the two transistors, the glowing rate or speed of the cigarette can be determined.

However, the known instrumentation allows only an integral measurement of the glowing speed. That is, an average speed is computed from the total time of glow and the predetermined path, and any interim changes in the glowing speed along this path cannot be ascertained.

However, in order to carry out quality control on various batches of cigarettes and comparisons between different products, time-changes in the glowing speed as well as the total duration of glow must be ascertained.

Further, the known instrumentation does not allow measuring the burning rate, i.e., the incandescent travel rate during the puff phases. There is increased conversion of the tobacco into smoke during the puff phases on account of ventilation, and hence the incandescent zone moves more rapidly, in superposition to the pure and slower glowing speed. This burning rate cannot be ascertained using the known, integrally measuring instrumentation.

SUMMARY OF THE INVENTION

It is, therefore, the object of the invention to create a process and equipment of the cited species which are free from the drawbacks mentioned.

In particular, a process and instrumentation are proposed to monitor and measure very accurately not only the glowing rate of the incandescent zone during the pauses between puffs, but also their combustion rate during the puff phases, that is, in a manner that is more than just time-averaged.

The advantages offered by the invention especially rest on the motion of the incandescent zone being continuously monitored and a signal corresponding to this motion being generated whereby the accurate correlation between the position of the incandescent zone and time is made possible. The travel rate of the incandescent zone at any point in the length of the smokable article can be easily obtained by differentiating the path-time curves whereby precise determinations are possible regarding the speeds of glow and/or burning of the article being investigated, in particular any changes in such speeds with time. For instance, it is possible to ascertain instantaneously whether the glowing and/or burning rates remain constant or vary in time.

Two basic methods are available for the sensor motion. In the first method, the sensor is moved continuously along with the incandescent zone and stopped only when a location with a precisely defined radiation intensity is reached. Practically, this means that the sensor is made to continuously follow the tip of the conical incandescent zone. Where the accuracy requirements are high, this method is only suitable for measuring the glowing rate, that is, for the motion of the incandescent zone during the pauses between puffs, but not for the determination of the rate of travel of burning, i.e., the motion of the incandescent zone during the puff phases.

In the course of a puff, tobacco will be burned essentially in the vicinity of the paper burning line, whereby the tip of the incandescent cone remains substantially in the same place. In this method, the sensor, therefore, remains stationary during the puff phase. Nevertheless, the overall speed of the motion of the incandescent cone determined over a relatively long time for the puff phase and the puff pause becomes larger than the glowing rate proper, that is, the speed without any puff phase.

As regards the other method, the sensor will be moved only when a site with a predetermined radiation intensity nears the incandescent zone. Practically, this means that the sensor in front of the incandescent zone is displaced toward the article mouthpiece. In this method, the speed of burning and/or glowing, that is, the speed of the incandescent zone for the puff phases and pauses, can be measured and recorded directly.

BRIEF DESCRIPTION OF THE DRAWINGS

The invention is discussed more comprehensively below in relation to illustrative implementations and referring to the attached schematic drawings.

DETAILED DESCRIPTION OF THE PREFERRED EMBODIMENT

Figure 1:
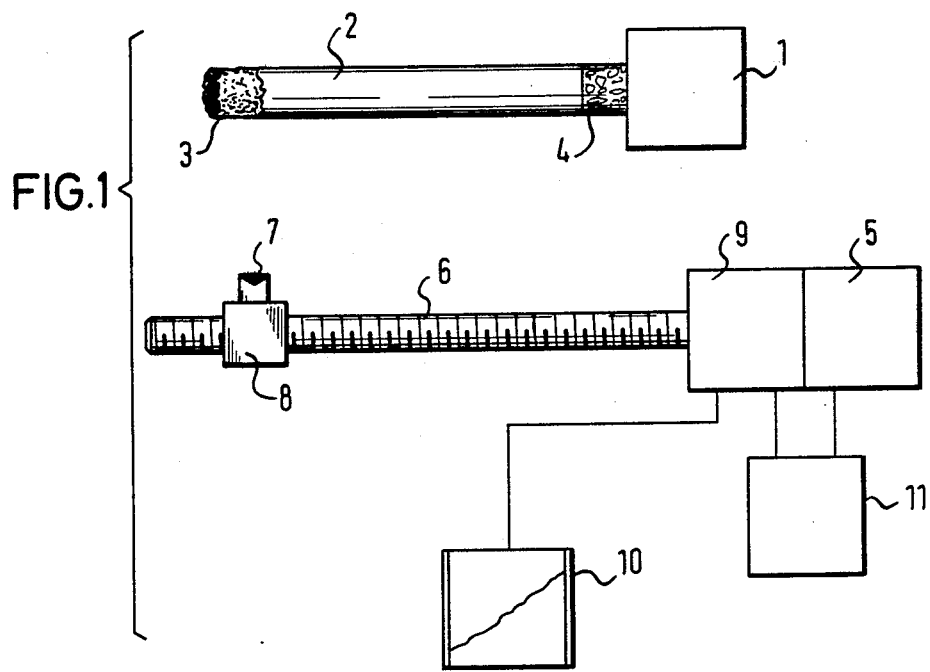
FIG. 1 is an overview sketch of the overall construction of an instrumentation for implementing the process of the invention.

As indicated by FIG. 1, a cigarette 2 is mounted in a cigarette smoking machine 1 which is operational. The incandescent cone 3 of the cigarette 2 moves toward the mouthpiece 4 in the course of smoking.

A threaded shaft 6 with a pitch such that about 10 threads extend across a length of 80 mm is driven by a motor 5 and is positioned parallel to the cigarette 2. A photodiode 7 for following the incandescent cone 3 of the cigarette 2 is mounted in a holding means 8 on the threaded shaft 6. A rotary potentiometer 9 is coupled to the motor 5 and generates a potential which depends on the advance of photodiode 7 and which can be plotted as a function of time by means of a path-time recorder 10. A common voltage supply 11 is coupled to the motor 5 and the potentiometer 9.

A switch S1 is connected in the circuit 12 of motor 5 by which the direction of rotation of motor 5 can be reversed or the motor stopped. Switch S1 is a three-pole switch, each pole being able to contact three stationary contacts, the contacts being denoted by A, B, C, A', B', C' and A", B", C", respectively.

Figure 2:
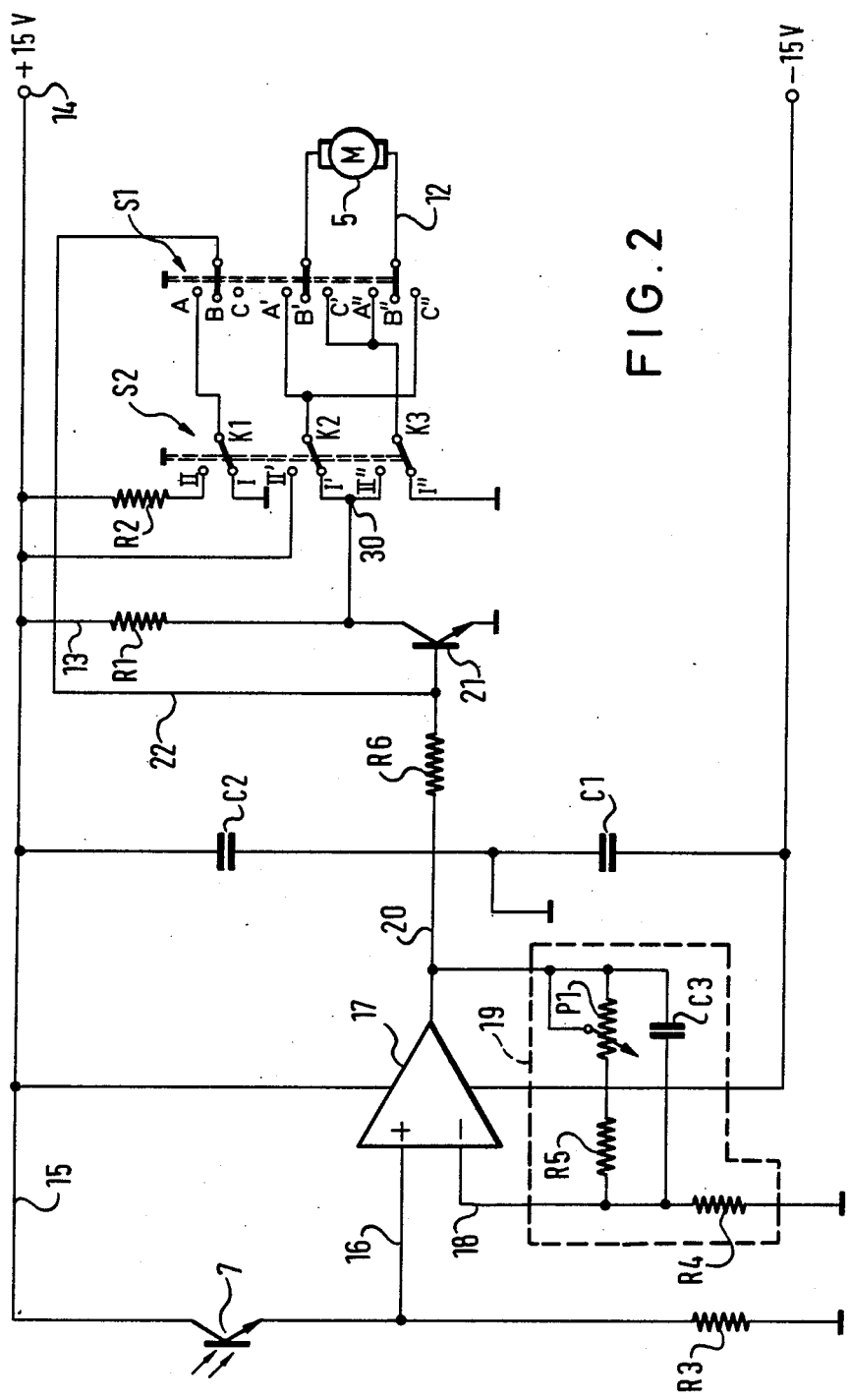
FIG. 2 is a circuit diagram of the electrical part of the instrumentation.

When the poles touch the lower contacts C, C' and C" in FIG. 2, the motor is turned on and runs in its normal direction of rotation, whereby the photodiode 7 of FIG. 1 moves from left to right on the threaded shaft 6.

If the poles make contact with the center contacts B, B' or B" of FIG. 2, the motor is turned off and the threaded shaft 6 cannot rotate.

If, lastly, the poles rest against the upper fixed contacts A, A' or A", the direction of rotation of the motor 5 is reversed. That is, the photodiode 7 in FIG. 1 is returned from the right-hand side to the left-hand initial position at the beginning of the cigarette.

A further switch S2 operates with switch S1, by means of which the basic operation of the instrumentation can be set in a manner explained below.

In particular, the two stationary contacts A' and C" of switch S1 are connected with a first pole K2 of switch S2, while the two stationary contacts C' and A" of switch S1 are connected to a further pole K3 of switch S2. Lastly, the contact A of switch S1 is connected to a third pole K1 of switch S1.

The upper pole K1 of switch S1 shown in FIG. 2 is connected to the stationary contact A and can be switched between a position I where it is grounded and a position II where it is connected through a resistor R2 to the positive terminal of a voltage source 14.

The center pole K2 can be switched between a position I' and a position II', where it is directly applied to the positive terminal of the voltage source 14. Lastly, the lower pole K3 of the switch S2 can be switched between a position I", where it is grounded and a position II". The two positions I' and II" are connected by a common point 30 which, in turn, passes through a resistor R1 and a line 13 to the positive terminal of the voltage source 14, and through the collector-emitter path of transistor 21 to ground. The base of transistor 21 is connected by a line 22 to the upper pole of switch S1. The two other poles of switch S1 are connected to motor 5.

Photodiode 7 is connected by one terminal through resistor R3 to ground and by the other terminal through a line 15 to the positive terminal of the voltage source 14. A line 16 between the resistor R3 and the photodiode 7 applies the photodiode output into the + input of a comparator 17, and a reference potential is applied through line 18 into the comparator's − input. The amplitude of the reference potential can be adjusted. The reference potential is set by a feedback circuit 19, which comprises resistors R4 and R5, a capacitor C3 and a potentiometer P1. The potentiometer P1 adjusts the reference potential. The output of comparator 17 is connected by a further resistor R6 and a line 20 to the base of transistor 21. The negative terminal 15 of the voltage source is connected through two capacitors C1 and C2 to the positive terminal.

For the lower position of the switch S2 as shown, the fixed contact I' is connected through line 13 and resistor R1 with the positive terminal of the voltage source 14, while contact I" is at ground.

The operation of the instrumentation of the invention shall now be discussed. After the cigarette 2 is placed into the smoking machine 1 and the smoking has begun, the photodiode 7 is moved back to the left-hand end of the threaded shaft 6 as shown in FIG. 1 by setting the switch S1 such that its poles contact the fixed contacts A, A' and A". When the left end is being reached, the switch S1 is switched so that its poles contact the stationary contacts C, C' and C", motor 5 rotating in its normal direction and the photodiode 7 is moved to the right. This motion of the photodiode is coupled with the rate of travel of the incandescent zone of cigarette 2 such that it will move to the right in relation to the motion of the incandescent zone. This "locking" of photodiode 7 to the incandescent zone of the cigarette 2 can be achieved in the two following ways as a function of the position of switch S2: if switch S1 is in the operational position and the poles of the second switch S2 contact the fixed contacts I, I' and I" as indicated in FIG. 2, the current passes from the positive terminal of the voltage source 14 through the resistor R1, the contacts I', C", the motor 5 and contacts C' and II" so that the motor 5 rotates and the photodiode 7 is displaced on the threaded shaft 6. When photodiode 7 arrives at a location where it is irradiated by the cigarette's incandescent zone at a predetermined precisely defined intensity, then the photodiode 7 becomes conductive; that is, hard-driving. Now a current can pass through the photodiode 7 which will be compared in comparator 17 with a reference value, the comparator generating an output signal when the voltage across R3 equals the reference value, said output signal being applied to the base of transistor 21 which then becomes conductive, whereby the current from line 13 no longer passes through the motor 5 but directly through the transistor 21, the motor 5 thereby being stopped. This results in the photodiode 7 no longer being displaced on the threaded shaft 6, whereby the photodiode 7 is locked to the incandescent zone of cigarette 2. Only after the generally conical incandescent zone 3 of the cigarette has left the response range of the photodiode 7 will the transistor 21 be blocking again and thereby the motor 5 started again.

Seen from the tip of the incandescent cone, the photodiode therefore is made to follow in this mode of operation.

When switching the switch S2 to the fixed contacts II, II' and II", with contacts II' and II" being connected through the motor 5, no current flows for a non-conducting photodiode 7. Therefore, the motor 5 does not rotate and photodiode 7 remains stationary.

Only when the incandescent cone 3 of the cigarette nears the response range of the photodiode 7 will the photodiode become conducting, whereby a signal is applied to the base of transistor 21 in the manner explained above, and this transistor is then conducting, thereby starting the motor 5 and the advance of the threaded shaft 6. In this mode of operation, the photodiode 7 therefore is displaced in front of the incandescent zone toward the mouthpiece.

The first method, that is, for the positions I, I' and I" of the poles of switch S2, is especially suited to determine the cigarette's glowing rate, i.e., the speed of the incandescent zone during the pauses between puffs, whereas the second method, that is, for the positions II, II' and II" of the poles of switch S2, is especially suited for ascertaining the cigarettes combustion and/or glowing rate as, during the puff phase, the tobacco where burning is substantially in the vicinity of the paper burning line and the tip of the incandescent cone remains substantially at the same position.

To allow a satisfactory reverse rotation of the motor 5 when the switch S2 is in the II position, the transistor 21 must be conducting. To that end, the feedback line 22, connected by contacts II and A to the positive terminal of the voltage source 14 is provided, which is further connected to the base of transistor 21.

The response range of the photodiode, i.e., the radiation intensity at which it responds, can be set by means of potentiometer P1.

Thus, using such instrumentation, both the rate of travel of the glow zone, that is, the displacement of the incandescent zone taking place without drawing on the cigarette by means of the natural burning process and the burning rate, that is, the speed with which the incandescent zone moves forward when there is drawing on the cigarette, can be determined.

Figure 3:
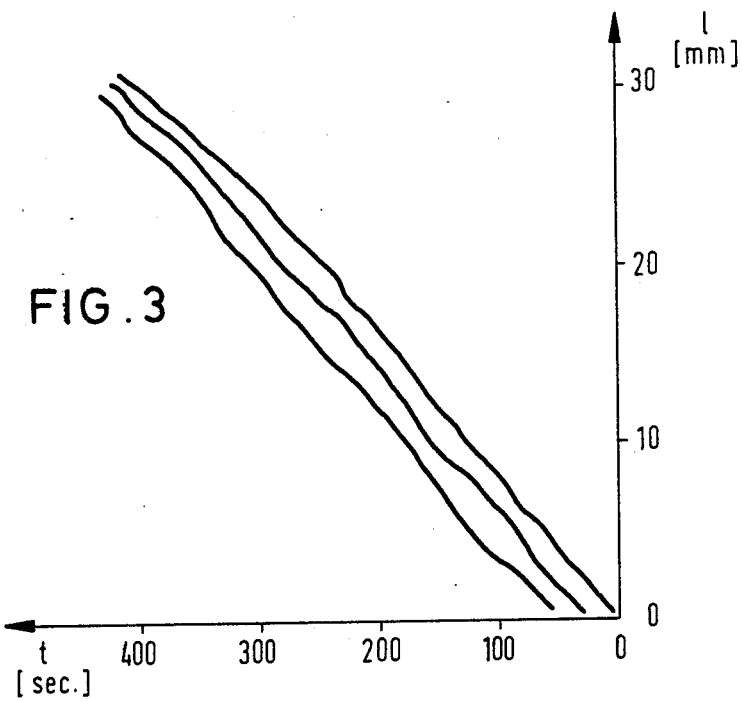
FIG. 3 is a family of curves recorded by means of the instrumentation, obtained from different cigarettes.

FIG. 3 schematically shows several test results obtained by the instrumentation of the invention. It is a family of pathtime plots for the incandescent cone of a cigarette, free from drawing. It is quite clear that the glowing rate over the entire length of the cigarette is not constant, rather that it varies with time.

The present invention may be embodied in other specific forms without departing from the spirit or essential characteristics thereof. The presently disclosed embodiments are, therefore to be considered in all respects as illustrative and not restrictive, the scope of the invention being indicated by the appended claims, rather than the foregoing description, and all changes which come within the meaning and range of equivalency of the claims are, therefore, to be embraced therein.

What is claimed:

1. An apparatus for determining the burning and/or glowing rate of a smokable article, said apparatus comprising:
   (a) sensor means for sensing the incandescent zone of the smokable article;
   (b) drive means for moving said sensor means along a path parallel to the direction of burning and glowing of the smokable article; and
   (c) control circuit means, including first switch means coupled to said sensor means and said drive means for stopping said drive means and thereby the movement of said sensor means when said sensor means detects a predetermined radiation intensity and for starting said drive means and thereby said sensor means when said sensor means detects a radiation intensity other than said predetermined intensity when said first switch means are in a first state, and for starting said drive means and thereby the movement of said sensor means when said sensor means detects a predetermined radiation intensity and for stopping said sensor means when said sensor means detects a radiation intensity other than said predetermined intensity when said first switch means are in a second state.

2. An apparatus as set forth in claim 1 wherein said sensor means is a photodiode which switches between non-conducting and conducting states upon the sensing of said predetermined radiation intensity.

3. An apparatus as set forth in claim 1 wherein said drive means comprises a motor and coupling means for coupling said motor to said sensor means wherein said coupling means converts the rotary output of said motor means to longitudinal movement of said sensor means.

4. An apparatus as set forth in claim 3 wherein said coupling means comprises a screw-threaded shaft and a screw threaded mounting means positioned thereon, said sensor means being mounted thereon.

5. An apparatus as set forth in claim 3 wherein said control circuit means includes second switch means for reversing the direction of motor rotation and thereby the direction of travel of said sensor means.

6. An apparatus as set forth in any one of claims 3–5 including potentiometer means coupled to said motor, the potential across said potentiometer means being varied as a function of the rotational motion of said motor and thereby the longitudinal travel of said sensor means.

7. An apparatus as set forth in claim 6 including recording means for recording the potential across said potentiometer means as a function of time.

* * * * *